United States Patent [19]

Cucinella et al.

[11] 4,122,108

[45] Oct. 24, 1978

[54] METHOD FOR THE PREPARATION OF ORGANIC ALUMINUM-IMIDES AND PRODUCTS OBTAINED THEREBY

[75] Inventors: Salvatore Cucinella; Tito Salvatori; Alessandro Mazzei, all of San Donato Milanese, Milan, Italy

[73] Assignee: Snamprogetti, S.p.A., San Donato Milanese, Italy

[21] Appl. No.: 757,228

[22] Filed: Jan. 6, 1977

[30] Foreign Application Priority Data

Jan. 9, 1976 [IT] Italy .............................. 19094 A/76
Apr. 22, 1976 [IT] Italy .............................. 22546 A/76

[51] Int. Cl.$^2$ ............................................. C07F 5/06
[52] U.S. Cl. ............................ 260/448 A; 260/448 R
[58] Field of Search ........................ 260/448 A, 448 R

[56] References Cited

U.S. PATENT DOCUMENTS

| | | | |
|---|---|---|---|
| 3,321,504 | 5/1967 | Fetter et al. ................... | 260/448 A |
| 3,651,024 | 3/1972 | Nelson et al. ................... | 260/448 R |
| 3,901,862 | 8/1975 | Cucinella et al. ............... | 526/163 X |
| 3,983,150 | 9/1976 | Casensky et al. ............... | 260/448 R |

OTHER PUBLICATIONS

Mole et al., Organoaluminum Compounds, Elsevier Publ. Co., Amsterdam, pp. 229–240 (1972).
Laubengayer et al., JAC S83, 542–546 (1961).
Laubengayer et al., Inorg. Chem. 1 (3), 632–637 (1962).
Ehrlich et al., Inorg. Chem. 3 (5), 628–631 (1964).
Cucinella et al., J. Organometallic Chem. 78, 185–201 (1974).
Cucinella et al., J. Organometallic Chem. 108, 13–25 (1976).
Cucinella et al., J. Organometallic Chem. 121, 137–147 (1976).

*Primary Examiner*—Helen M. S. Sneed
*Attorney, Agent, or Firm*—Morgan, Finnegan, Pine, Foley & Lee

[57] ABSTRACT

Novel organic aluminum imides, highly resistant to oxidation and moisture and useful for polymerization and alkylation reactions, are prepared by reacting a poly(N-alkyliminoalane) with an aluminum alkyl, or with a halogen acid and then with an alkyl derivative of an alkali metal.

13 Claims, No Drawings

METHOD FOR THE PREPARATION OF ORGANIC ALUMINUM-IMIDES AND PRODUCTS OBTAINED THEREBY

This invention relates to a novel method for the preparation of organic aluminum imides, compounds which can be employed as polymerization or alkylation agents, especially for reactions at high temperatures.

It is known that organic aluminum imides having the formula $(R.Al.N.R')_n$, wherein R and R', equal or different, are alkyls, cycloalkyls, or aryls and $n$ is the number of repetitive units, can be obtained by reacting organic metallic compounds of aluminum having the formula $AlR_3$ with primary amines.

However, the methods known heretofore provide only for the obtention of tetramers, that is with $n = 4$, with the exception of the case of methylamine which gives a heptamer and an octamer by reaction with $Al(CH_3)_3$ or $Al(C_2H_5)_3$, respectively.

We have now found, and this is the subject-matter of the present invention, a novel method of preparation which permits to obtain organic aluminum imides containing respective units of the above mentioned type with $n$ greater than 4 also in the case of primary amines which are higher homologs of methylamine.

According to the present invention, such a result can be achieved by reacting a poly(N-alkyliminoalane) of the formula $(H.Al.N.R')_n$ with trialuminum alkyls $Al.R_3$, the radicals R and R' have the same meanings as defined above and $n$ being a number equal to 4 or higher.

It is well known, from copending patent applications in the name of the same Applicants hereof, that the poly(N-alkyliminoalanes) are formed by —HAlNR— units bound to each other to form a cage-like structure and that the number of such units $n$ (variable from 4 to 10) in such cage-structures depends both from the nature of the starting amine, and the method of preparation.

In the exchange reaction with aluminum, the pre-existing oligomerization degree of the starting PIA remains unaltered.

Thus, in the as-obtained alkyl compounds, $(RAlNR')_n$ the value of $n$ (equal to 4 or higher) is the same as in the initial hydride derivative.

Consistently with the molar ratio $PIA/AlR_3$ put to react, it is possible to carry out the complete substitution, or a partial substitution only, of the hydride hydrogens with alkyl radicals. In this way, in addition to completely alkylated iminic derivatives, derivatives can be obtained which simultaneously contain hydride bonds, Al-H, alkyl-bonds, Al-R in the same molecule.

It is thus possible to have derivatives having a reducing power (or alkylating power) which is controlled and which are interesting from a practical standpoint.

This is a second object of the present invention, which is closely bound to the claimed method, and which cannot be achieved with the conventional procedures.

The above indicated compounds have the general formula:

$$[(R.Al.NR')_m(H.Al.N.R')_x]$$

wherein R and R' have the meanings indicated above, the sum $(m + x)$ equals $n$, with $m$ variable between 1 and $n$, and $x$ variable between $(n - 1)$ and 0.

The thusly obtained novel compounds are characterized by a high heat stability, higher than that of the known aluminum-alkyl compounds and exhibits, in addition, a surprising stability to air if compared with the well known high reactivity of the aluminum-carbon bond of other organic compounds of aluminum with respect to oxygen or moisture, which are responsible for the violent reactions which are observed whenever compound of this kind come into contact with air.

A second object of the present invention is the synthesis of PIA which are either partially or completely alkylated through a process in two steps which comprises a preliminary substitution of the hydride hydrogens by halogen atoms and subsequent treatment of the as-obtained product with alkyl derivatives of alkali metals.

The end product retains the typical cage structure of the starting PIA.

The reaction of the first stage is carried out starting from the PIA concerned and a halide or a halogen acid according to the pattern:

wherein R' and $n$ have the same meanings as defined above, HX is a halogen acid, $p$ is the number of moles employed and can be equal to or lower than the degree of oligomerization, $n$, of the PIA.

Subsequently, the as-obtained product is reacted with an alkyl derivative of an alkali metal:

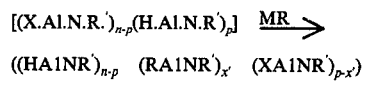

wherein $x'$ is comprised between 1 and $n$, $n$ being always the sum of the three iminic units which have differently been substituted.

It is thus apparent that it is possible to obtain both the products described in the main application and those which simultaneously contain aluminum-halogen bonds, aluminum-hydrogen-bonds and aluminum-alkyl bonds in the same molecule.

The above mentioned compounds maintain in any case the structures of the starting PIA unaltered.

EXAMPLE 1

Synthesis of $(CH_3AlN\text{-iso }C_3H_7)_6$

To a solution of 82.5 millimols of $Al(CH_3)_3$ in 70 mls of benzene, which has been heated to 50° C., and stirred, there is slowly added a solution of 3.3 millimols of $(H\ Al\ N\text{—iso }C_3H_7)_6$ in 30 mls benzene in a nitrogen atmosphere. The mixture is refluxed for 7 hrs. and then kept at room temperature during 18 hours, the result being the formation of a white crystalline compound which is insoluble and is separated by filtering it off, dried (10 hours, $10^{-3}$ mmHg, room temp.) and analyzed (yield:- gram 1.7).

| For $C_4H_{10}AlN$ | Al% | N% |
|---|---|---|
| Calcd. | 27.2 | 14.1 |
| Found | 26.6 | 13.3 |

The mass spectrum is characterized by the presence of an intense $(N-CH_3)^+$ ion at $m/e = 579$ which can be attributed to the hexamer (CH$_3$Al N iso-C$_3$H$_7$)$_6$. The compound is stable to temperatures up to 375° C.

EXAMPLE 2

Synthesis of a co-crystallization product of (Ch$_3$Al N iso C$_3$H$_7$)$_6$ with [(CH$_3$Al n-iso C$_3$H$_7$)$_5$. (H Al N-iso C$_3$H$_7$)$_1$]

To a stirred solution of 1.7 millimol of (H Al N iso-C$_3$H$_7$)$_6$ in 25 mls of benzene there has been slowly added a solution of 10 millimols of Al(CH$_3$)$_3$ in 25 mls of benzene at room temperature, working in a nitrogen atmosphere.

The mixture is refluxed for 9 hrs. and then allowed to stand for 18 hrs. A formation is noted of colorless prismatic crystals which are filtered off, dried and analyzed. Yield: 0.9 grams.

| For C$_{47}$H$_{118}$Al$_{12}$N$_{12}$ | Al% | N% |
|---|---|---|
| calcd. | 27.5 | 14.3 |
| found | 26.9 | 14.1 |

The mass spectrum is characterized by the presence of intense (N-CH$_3$)$^+$ ions at m/e = 579 and 565, which can be attributed, respectively, to the hexamers (CH$_3$Al N-iso C$_3$H$_7$)$_6$ and [(CH$_3$AlN - iso C$_3$H$_7$)$_5$. (H Al N iso C$_3$H$_7$)$_1$].

The relative intensities of the two ions is in agreement with the formation of the two compounds in equimolecular quantities. The compound is stable to temperatures up to 340° C.

EXAMPLE 3

Synthesis of [(C$_2$H$_5$Al N-iso C$_3$H$_7$)$_4$.(H Al N-iso C$_3$H$_7$)$_2$]

To a stirred solution of 1.7 millimols of (H Al N-iso C$_3$H$_7$)$_6$ in 25 mls benzene has been slowly added a solution of 10 millimols of Al (C$_2$H$_5$)$_3$ in 25 mls benzene at room temperature, working in a nitrogen atmosphere.

The solution is refluxed for 9 hrs. and allowed to stand at room temperature for 18 hrs.

On the reaction solution the mass spectrometry detects the formation of [(C$_2$H$_5$AlN-isoC$_3$H$_7$)$_4$.(HAlN-iso C$_3$H$_7$)$_2$]

Crystals of such compound have been separated by cooling at −5° C. of the as-obtained solution by removing the reaction benzene by evaporation under reduced pressures and redissolving the residue with 15 mls hexane.

The crystals have been separated by filtering them off, dried and analyzed.

| For C$_{26}$H$_{64}$Al$_6$N$_6$ | Al% | N% |
|---|---|---|
| Calcd. | 26.0 | 13.5 |
| Found | 26.1 | 12.6 |

The mass spectrum is characterized by the presence of (M-Me)$^+$ ions at m/e = 607 and (M-Et)$^+$ at m/e = 593, which can be attributed to the hexamer [(C$_2$H$_5$AlN-isoC$_3$H$_7$)$_4$.HAlN-isoC$_3$H$_7$)$_2$]. The compound is stable to temperatures up to 335° C.

EXAMPLE 4

Synthesis of (CH$_3$Al N-isoC$_3$H$_7$)$_4$

A stainless steel autoclave of the capacity of one liter is charged, in the order given, with a solution of 370 millimols of Al(CH$_3$)$_3$ in 300 mls toluene and a solution of 370 millimols of isoC$_3$H$_7$NH$_2$ in 50 mls of toluene under a nitrogen blanket. The mixture is stirred with a rotary mechanical stirrer at 210° C. for 50 hours.

On the reaction solution, the mass spectrometry has indicated the presence of (CH$_3$AlN-isoC$_3$H$_7$)$_4$ as the single reaction product.

Flake crystals are easily formed from the solution in hexane of the residue when the reaction solvent is evaporated off. The crystals have been filtered off and analyzed.

| For C$_4$H$_{10}$AlN | Al% | N% |
|---|---|---|
| Calcd. | 27.2 | 14.1 |
| Found | 26.8 | 14.0 |

The mass spectrum is characterized by a weak molecular ion M$^+$ at m/e = 396 and by an intense (M-Me)$^+$ ion at m/e = 381 which can be attributed to the tetramer (CH$_3$AlN-isoC$_3$H$_7$)$_4$.

In agreement with a cubic structure, the $^1$HNMR in benzene $^1$HNMR' shows the equivalence of both the groups CH$_3$ bound to aluminum and of the isopropyl groups bound to nitrogen: the spectrum exhibits a singlet at 10.11 $\tau$ (protons of the CH$_3$ bound to Al), a doublet at 8.80 $\tau$ (CH$_3$ of the group isoC$_3$H$_7$), a septet at 6.37 $\tau$ (CH of the group isoC$_3$H$_7$). The compound is decomposed at 225° C.

EXAMPLE 5

Synthesis of (C$_2$H$_5$Al N-isoC$_3$H$_7$)$_4$

A stainless steel autoclave of the capacity of one liter is charged in the order given with a solution of 300 millimols of Al(C$_2$H$_5$)$_3$ in 250 mls toluene and a solution of 300 millimols of isoC$_3$H$_7$NH$_2$ in 50 mls toluene, under a nitrogen blanket.

The mixture is stirred during 50 hours at 210° C. On the reaction solution, the mass spectrometry indicates the exclusive formation of (C$_2$H$_5$AlN-isoC$_3$H$_7$)$_4$.

The reaction solvent has been removed by evaporating it off under reduced pressures, the residue has been redissolved in 250 mls of hexane and the solution has been cooled to −78° C.

A white solid is formed, which has been separated by decantation, washed with fresh solvent, dried and analyzed. (Yield: 3.1 grams).

| For C$_5$H$_{12}$AlN | Al% | N% |
|---|---|---|
| calcd. | 23.8 | 12.4 |
| Found | 23.7 | 12.5 |

The mass spectrum is characterized by a weak molecular ion M$^+$ at m/e 452 and by (M-Me)$^+$ ions at m/e 437 and (M-Et)$^+$ at m/e 423 which can be attributed to the tetramer (C$_2$H$_5$AlN-isoC$_3$H$_7$)$_4$.

In agreement with a cubic structure, the $^1$HNMR in benzene exhibits the equivalence both of groups C$_2$H$_5$ bound to aluminum, and of the isopropyl group bound to nitrogen. The spectrum exhibits a quartet at 9.57$\tau$(protons of the CH$_2$'s bound to aluminum), a triplet at 8.54 $\tau$ (CH$_3$ ofthe C$_2$H$_5$), a doublet at 8.74 $\tau$ (CH$_3$ of isoC$_3$H$_7$), a septet at 6.60 $\tau$ (CH of isoC$_3$H$_7$).

EXAMPLE 6

A mixture of [(Cl Al N isoC$_3$H$_7$) (H Al N -iso C$_3$H$_7$)$_5$] (III) and [(Cl Al N-isoC$_3$H$_7$)$_2$.(H Al N-iso C$_3$H$_7$)$_4$] (IV) (9.5 milligramatoms of Cl in total) solubized in diethyl ether (70 mls) is supplemented with a solution of LiC$_2$H$_5$ (9.6 millimols) in diethyl ether (30 mls) and the solution is stirred at the reflux temperature for 1 hour and one half.

The as-formed LiCl is filtered off and the reaction product is characterized by means of the mass spectrometry which indicates the complete replacement in (III) and (IV) of the chlorine atoms by ethyl groups.

| Compound | (M-CH$_3$)$^+$ m/e | (M-Et)$^+$ m/e |
|---|---|---|
| [(C$_2$H$_5$AlN-isoC$_3$H$_7$) . (HAlN-iso C$_3$H$_7$)$_5$] | 523 | 509 |
| [(C$_2$H$_5$AlN-isoC$_3$H$_7$)$_2$ . (HAlN-iso C$_3$H$_7$)$_4$] | 551 | 537 |

EXAMPLE 7

To a suspension of (ClAlN-iso-C$_3$H$_7$)$_6$ (V) (3.5 millimols) in diethyl ether (100 mls.) is added a solution of LiCH$_3$ (42 millimols) in diethyl ether (50 mls).

The mixture is kept stirred at the reflux temperature for 16 hrs.

The reaction product is characterized by means of mass spectrometry which indicates the formation of a mixture of products deriving from (V) by partial or complete substitution of chlorine atoms by methyl groups.

| Product | M-CH$_3$)$^+$ | m/e | |
|---|---|---|---|
| [(CH$_3$AlN-isoC$_3$H$_7$)$_4$ . (ClAlN-iso C$_3$H$_7$)$_2$] | 619 | 621 | 623 |
| [(CH$_3$AlN-iso-C$_3$H$_7$)$_5$(ClAlN-iso C$_3$H$_7$)] | 599 | 601 | |
| [(CH$_3$AlN-iso-C$_3$H$_7$)$_6$] | 579 | | |

The product [(CH$_3$AlN-isoC$_3$H$_7$)$_6$] is by far predominant over the others.

What we claim is:

1. Organic aluminum imides having the formula:

$$((RAlNR')_m (HAlNR')_x)$$

wherein R and R' are the same or are different and are selected from the group consisting of alkyl, aryl, and cycloalkyl; the sum of $m + x$ is equal to $n$, and $n$ being a number equal to 4 or higher with $m$ being variable between 1 and $n$; $x$ is variable between $n-1$ and 0.

2. The organic imide of claim 1 wherein R is CH$_3$; R' is iso CH$_3$H$_7$; $m$ is 6 and $x$ is 0.

3. The organic imide of claim 1 wherein R is CH$_3$; R' is iso C$_3$H$_7$; $m$ is 5 and $x$ is 1.

4. The organic imide of claim 1 wherein R is C$_2$H$_5$; R' is iso C$_3$H$_7$; $m$ is 4 and $x$ is 2.

5. The organic imide of claim 1 wherein R is CH$_3$; R' is iso C$_3$H$_7$; $m$ is 4 and $x$ is 0.

6. The organic imide of claim 1 wherein R is C$_2$H$_5$; R' is iso C$_3$H$_7$; $m$ is 4 and $x$ is 0.

7. A method for the preparation of organic aluminum imides, having the formula:

$$((R Al NR')_m (H Al NR')_x)$$

wherein R and R' are the same or are different and are selected from the group consisting of alkyl, aryl and cycloalkyl; the sum of $m + x$ is equal to $n$, and $n$ being a number equal to 4 or higher with $m$ being variable between 1 and $n$; $x$ is variable between $n-1$ and 0 said method comprising the step of reacting a poly(N-alkyliminoalane) of the formula (HAlNR')$_n$, wherein $n$ is a number equal to 4 or higher, and R' is selected from the group consisting of alkyl, aryl and cycloalkyl, with a compound of the formula AlR$_3$ wherein R is selected from the group consisting of alkyl, aryl and cycloalkyl.

8. A method for the preparation of organic aluminum imides according to claim 7 said method comprising the step of reacting a poly(N-alkyliminoalane) of the formula (HAlNR')$_n$ with a compound of aluminum having the formula AlR$_3$ wherein R is alkyl.

9. The method of claim 7 wherein the poly(N-alkyliminoalane) is (HAlN iso C$_3$H$_7$)$_6$ and the AlR$_3$ compound is Al(CH$_3$)$_3$.

10. Organic aluminum imides having the formula:

$$(HAlNR')_{n-p}(RAlNR')_{x'} (XAlNR')_{p-x'}$$

wherein R and R' are the same or are different and are selected from the group consisting of alkyl, aryl and cycloalkyl; $p$ is the number of moles employed and is equal to or lower than the degree of oligomerization $n$; and $n$ is equal to 4 or higher $x'$ is between 1 and $n$ and X is halogen.

11. Organic aluminum imide according to claim 10 wherein R is C$_2$H$_5$; R' is iso-C$_3$H$_7$; $p$ is 1; and $n$ is 6.

12. Organic aluminum imide according to claim 10 wherein R' is iso C$_3$H$_7$; $p$ is 2 and $n$ is 6.

13. A method for the preparation of organic aluminum imides having the formula:

$$(HAlNR')_{n-p} (RAlNR')_{x'} (XAlNR')_{p-x'} {}_{pg.17}$$

wherein R and R' are the same or are different and are selected from the group consisting of alkyl, aryl and cycloalkyl; $p$ is the number of moles employed and is equal to or lower than the degree of oligomerization $n$; and $n$ is equal to 4 or higher, X is halogen, $x'$ is between 1 and $n$ said method comprising the steps of reacting polyiminoalanes of the formula (HAlNR)$_n$ with a halogen acid to obtain an intermediate product; contacting said intermediate product with an alkyl derivative of an alkali metal to obtain the product.

* * * * *